(12) United States Patent
Pruckner

(10) Patent No.: US 9,918,805 B2
(45) Date of Patent: *Mar. 20, 2018

(54) MEDICAL OR DENTAL HANDPIECE

(71) Applicant: W&H Dentalwerk Bürmoos GmbH, Bürmoos (AT)

(72) Inventor: Christian Pruckner, Vienna (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/377,023

(22) Filed: Dec. 13, 2016

(65) Prior Publication Data

US 2017/0086942 A1    Mar. 30, 2017

Related U.S. Application Data

(63) Continuation of application No. 14/693,201, filed on Apr. 22, 2015, now Pat. No. 9,603,675, which is a (Continued)

(30) Foreign Application Priority Data

Nov. 5, 2012 (EP) .................................... 12191193
Dec. 4, 2012 (EP) .................................... 12195365

(51) Int. Cl.
*A61C 1/00* (2006.01)
*A61C 1/05* (2006.01)
(Continued)

(52) U.S. Cl.
CPC .............. *A61C 1/003* (2013.01); *A61B 17/00* (2013.01); *A61B 90/30* (2016.02); *A61C 1/05* (2013.01);
(Continued)

(58) Field of Classification Search
CPC ........... A61C 1/003; A61C 1/05; A61C 1/088; A61B 17/00
See application file for complete search history.

(56) References Cited

U.S. PATENT DOCUMENTS 4,493,643 A    1/1985   Tachibana
4,568,642 A    2/1986   DeForrest et al.
(Continued)

FOREIGN PATENT DOCUMENTS

GB    1371525    10/1974
JP    60203247   10/1985
(Continued)

OTHER PUBLICATIONS

European Search Report for EP 07008056 (dated Aug. 8, 2007).
European Search Report for EP 08007019 (dated Aug. 14, 2008).

*Primary Examiner* — Robert N Wieland
(74) *Attorney, Agent, or Firm* — Klarquist Sparkman, LLP

(57) ABSTRACT

Embodiments of a medical or dental handpiece are disclosed. A medical or dental handpiece may include a rotatable drive element to drive a tool that can be connected to the handpiece, a rotational speed measuring device which is designed to generate a variable electric rotational speed measurement signal assigned to the rotational speed of the drive element, a lighting device that can be supplied with electric power for emitting radiation, in particular visible light, onto a treatment site, and at least one shared electric line, which is provided for transmitting electric power to the illumination device and the rotational speed measurement signal of the rotational speed measurement device. Further a corresponding method for the operation of a medical or dental handpiece is disclosed.

19 Claims, 2 Drawing Sheets

Related U.S. Application Data continuation of application No. PCT/EP2013/072970, filed on Nov. 5, 2013.

(51) Int. Cl.
    *A61C 1/08*      (2006.01)
    *A61B 17/00*      (2006.01)
    *A61B 90/30*      (2016.01)

(52) U.S. Cl.
    CPC .... *A61C 1/088* (2013.01); *A61B 2017/00084* (2013.01)

(56) References Cited

U.S. PATENT DOCUMENTS

| | | |
|---|---|---|
| 4,642,738 A | 2/1987 | Meller |
| 4,725,232 A | 2/1988 | Hatakeyama |
| 5,267,129 A | 11/1993 | Anderson |
| 5,364,227 A * | 11/1994 | Franetzki ............... A61C 1/05 415/35 |
| 5,457,611 A | 10/1995 | Verderber |
| 5,507,642 A | 4/1996 | Wohlgemuth |
| 5,800,172 A | 9/1998 | Goldenberg |
| RE36,917 E | 10/2000 | Leininger |
| 6,186,784 B1 | 2/2001 | Bailey |
| 6,270,342 B1 | 8/2001 | Neuberger et al. |
| 6,906,466 B2 | 6/2005 | Feng |
| 7,095,142 B2 | 8/2006 | Leininger |
| 2008/0261172 A1 * | 10/2008 | Rauchenzauner ....... A61C 1/05 433/132 |
| 2010/0055642 A1 | 3/2010 | Rothenwaender et al. |
| 2010/0109644 A1 | 5/2010 | Pruckner et al. |
| 2012/0115101 A1 | 5/2012 | Rauchenzauner et al. |

FOREIGN PATENT DOCUMENTS

| | | |
|---|---|---|
| JP | 60-253437 | 12/1985 |
| JP | 61-8042 | 1/1986 |
| JP | 2004-248991 | 9/2004 |
| JP | 2005-518865 | 6/2005 |
| JP | 2010-264233 | 11/2010 |
| WO | WO01/12095 | 2/2001 |

* cited by examiner

United States Patent US 9,918,805 B2

MEDICAL OR DENTAL HANDPIECE

CROSS REFERENCE TO RELATED APPLICATION

This is a continuation of U.S. patent application Ser. No. 14/693,201, filed Apr. 22, 2015, now U.S. Pat. No. 9,603, 675, which is a continuation of International Application No. PCT/EP2013/072970, filed Nov. 5, 2013, which was published in German under PCT Article 21(2), which in turn claims the benefit of abandoned European Patent Application No. EP 12191193.7, filed Nov. 5, 2012, and European Patent Application No. EP 12195365.7, filed Dec. 4, 2012, now European Patent No. 2727552. All of the prior applications are incorporated herein by reference.

BACKGROUND

Field

The present invention relates to a medical or dental handpiece having a rotational speed measuring device for measuring the rotational speed of a drive element of the handpiece that can be connected to a tool.

Description of Prior Art

U.S. Pat. No. 4,493,643 discloses such a medical or dental handpiece having a rotational speed measuring device arranged in a head section of the handpiece.

SUMMARY

It is an object to optimize the implementation or the installation situation of the rotational speed measuring device, in particular of a rotational speed sensor on the handpiece, preferably in the head section of the handpiece, so that the rotational speed measuring device, in particular the rotational speed sensor, can be arranged and operated in the handpiece, in particular in or adjacent the head section of the handpiece, despite the large number components and the very limited available space.

This object is achieved by a medical or dental handpiece comprising: a drive element that can be induced to rotate for driving a tool that can be connected to the handpiece, a rotational speed measuring device that is designed to generate a variable electric rotational speed measurement signal assigned to the rotational speed of the drive element, a lighting device that can be supplied with electric power for emitting radiation, in particular visible light, onto a treatment site and at least one shared electric line, which is provided for transmitting the electric power (the electric power supply signal) to the lighting device and the rotational speed measurement signal of the rotational speed measuring device.

Thus, advantageously a shared electric signal line or electric power supply fine is created for the rotational speed measuring device, in particular for the rotational speed sensor, and for the lighting device so that the electric measurement signals of the rotational speed measuring device and the electric (power supply) signals of the lighting device can be conducted over said line. This eliminates the need to provide a separate electric line and separate electric connections for the rotational speed measuring device and the lighting device, so that the space available in the interior of the handpiece is utilized more effectively, and furthermore, the design of the handpiece, in particular in the coupling region, is simplified.

The rotational speed measuring device is preferably designed as an inductive rotational speed measuring device or comprises an inductive rotational speed sensor. The inductive rotational speed sensor or the inductive rotational speed measuring device preferably comprises a magnetic element and at least one measuring coil, which can be moved relative to one another. In particular the magnetic element is arranged on or attached to the drive element for driving a tool that can be connected to the handpiece, for example, an impeller. The measuring coil is preferably connected to or attached to a component of the handpiece which is rotationally fixed with respect to the drive element, for example, the outer sleeve. Preferably the inductive rotational speed measuring device additionally comprises at least one soft magnetic element to concentrate the magnetic field of the magnetic element. The soft magnetic element is provided in or on the measuring coil in particular. The inductive rotational speed measuring device is designed in particular to generate an electric rotational speed measurement signal, which is designed as an alternating signal, for example, as a sinusoidal or pulse-shaped electric alternating signal or alternating current signal.

The handpiece may clearly also have an alternative rotational speed measuring device or an alternative rotational speed sensor, which are designed, for example, as a capacitive or optical rotational speed measuring device or rotational speed sensor or as a rotational speed measuring device by means of eddy currents and which generate in particular an electric rotational speed measurement signal. The optical rotational speed measuring device comprises, for example, a radiation source, at least one reflector that is provided on the drive element for the light that can be emitted by the radiation source and a receiving device for the radiation reflected by the reflector. A capacitive rotational speed measuring device comprises, for example, a capacitor and an element provided on the drive element for changing the capacitance of the capacitor. A rotational speed measuring device or a rotational speed sensor, which does not directly generate an electric rotational speed measurement signal, for example, an optical rotational speed sensor, is preferably connected to a converter device, for example, an electronic converter, which converts the rotational speed measurement signal, for example, an optical signal, into an electric rotational speed measurement signal.

The lighting device and at least a part of the rotational speed measuring device, in particular the at least one measuring coil of the inductive rotational speed measuring device, are preferably arranged electrically in series. The electric power (the electric power supply signal) is or will thus be supplied to the lighting device over at least a portion of the rotational speed measuring device, in particular over the at least one measuring coil of the inductive rotational speed measuring device. The measuring coil is preferably designed as a low-resistance measuring coil.

The drive element is preferably mounted rotatably in the handpiece by means of at least one hearing, in particular a roller bearing. The drive element is in particular preferably designed as an impeller, which can be driven or induced to rotate by a compressed gas. Alternatively, the drive element is designed as a shaft or a hollow shaft that can be induced to rotate.

The lighting device for emitting radiation onto a treatment site preferably comprises one or more, for example, three, four or five optical semiconductor elements, in particular light-emitting diodes (LEDs). However, the lighting device may clearly also have other radiation sources, for example, at least one incandescent bulb or at least one gas discharge lamp. The lighting device, in particular the at least one optical semiconductor element, is preferably arranged either on the head section of the handpiece, in particular around a tool receptacle opening on the headpiece, or adjacent to the head section. The lighting device is provided in particular on the side of the handpiece, on which a tool receptacle opening of the handpiece is situated. The lighting device is designed in a ring shape in particular, preferably surrounding the tool receptacle opening of the head section. The tool can be connected to the drive element in particular through an internal bore of the ring-shaped lighting device, for example, being insertable into or removable from a tool mount on the handpiece. At least one opening and/or one channel through which a fluid, in particular a cooling medium, for example, a water-air mixture can be dispensed in the direction of the treatment site is preferably provided in or on the body of the lighting device.

The shared electric line provided in the handpiece, comprising one or more line wires, for example, connects the lighting device to an electric power source, in particular to a constant current source and/or a constant voltage source. The shared electric line provided in the handpiece also connects in particular at least a part of the rotational speed measuring device, for example, its measuring coil, to the electric power source, in particular to the constant current source and/or to the constant voltage source, or the lighting device via at least a part of the rotational speed measuring device, for example, its measuring coil, to the electric power source. The shared electric line provided in the handpiece is provided for shared and preferably simultaneous transmission of electric signals of two different electric power sources, in particular of the electric power source (constant current source and/or constant voltage source) for supplying power to the lighting device with a substantially constant electric signal and the rotational speed measuring device. The two electric signals, for example, the electric power supply signal for the lighting device and the rotational speed measurement signal in particular form a mixed electric signal.

The electric power source, for example, a constant current source and/or a constant voltage source, is designed to supply the lighting device with a substantially constant electric signal, in particular with a constant current or a d.c. current or a d.c. voltage. If, according to one embodiment, exclusively a constant voltage source (and not a constant current source) is provided as the electric power source, then the lighting device comprises, for example, an incandescent bulb or an optical semiconductor element, for example, a light-emitting diode having a series resistor. The electric power source may be arranged in the handpiece or may be provided outside of the handpiece, for example, in an adaptor or coupling part that can be connected to the handpiece or in a supply unit or in a control unit and/or regulating unit. Thus, according to one embodiment, a medical or dental treatment device is created having a handpiece with a shared electric line for transmission of the electric power (the power supply signal) to the lighting device and for transmission of the electric rotational speed measurement signal of the rotational speed measuring device and an electric power source for supplying power to the lighting device, wherein the handpiece and the electric power source are preferably detachable from one another. The electric power source, which is provided in the handpiece in particular, comprises a battery, an accumulator or a generator, for example, which is preferably connected to an electric rectifier.

The electric power source preferably comprises a constant current source or a constant voltage source, which is designed to receive a mixed electric signal which comprises the variable electric rotational speed measurement signal which is generated by the rotational speed measuring device and is assigned to the rotational speed of the drive element and to correct this variable electric rotational speed measurement signal by means of a first variable electric correction signal, such that the substantially constant electric signal is available for the power supply to the lighting device. The variable electric rotational speed measurement signal comprises in particular a sinusoidal or pulse-shaped electric signal generated by the rotational speed measuring device. The mixed electric signal additionally comprises in particular the substantially constant electric signal for the power supply to the lighting device, which is supplied by the constant current source or the constant voltage source. In other words, two electric power sources (the constant current source or the constant voltage source and the rotational speed measuring device) are thus provided, their electric signals (the constant electric signal and the variable electric rotational speed measurement signal) being superimposed and forming the mixed electric signal, and their electric signals being transmitted or transmissible, in particular simultaneously, over the shared electric line.

The constant current source or the constant voltage source is designed as an electric or electronic regulating device in particular. The constant current source or constant voltage source is preferably designed to generate a first variable electric correction signal to make available the substantially constant electric signal to the lighting device. The constant current source or the constant voltage source is thus preferably designed to generate a first variable sinusoidal or pulse-shaped electric correction signal, which counteracts or equalizes the variable electric rotational speed measurement signal of the mixed electric signal or the variable component of the mixed electric signal.

According to one embodiment, the medical or dental treatment device comprises an evaluation unit, which is designed to determine the rotational speed of the drive element on the basis of the variable electric rotational speed measurement signal or the first variable electric correction signal of the constant current source or the constant voltage source. The evaluation unit is preferably connected (electrically) to the constant current source or the constant voltage source and/or at least one part of the rotational speed measuring device, in particular the measuring coil of the inductive rotational speed measuring device. The evaluation unit is preferably designed to detect or receive the variable electric rotational speed measurement signal or the first variable electric correction signal of the constant current source or of the constant voltage source and in particular to determine the rotational speed of the drive element on the basis of the frequency of one of these two signals. The frequency of the correction signal corresponds to or represents the frequency of the rotational speed measurement signal of the rotational speed measuring device. The evaluation unit comprises a microcontroller in particular. The evaluation unit preferably comprises at least one device for processing the variable electric rotational speed measurement signal or the first correction signal, for example, an analog-digital converter or a signal filter.

The medical or dental treatment device preferably comprises a control unit and/or regulating unit, which is designed to control and/or regulate the rotational speed of the drive element on the basis of the rotational speed determined by the evaluation unit, in particular such that the drive element can be operated at a constant rotational speed. The control unit and/or regulating unit preferably comprises and/or controls and/or regulates an adjusting element, for example, a valve, in particular a solenoid valve, which is designed to act on the compressed gas driving the drive element, for example, the impeller. The adjusting element adjusts the flow rate and/or the gas pressure of the compressed gas for driving the drive element in particular. The control unit and/or regulating unit comprise(s) a microcontroller in particular. A shared microcontroller comprising the evaluation unit and the control unit and/or regulating unit is preferably provided.

According to one embodiment, a temperature sensor, which is designed to generate a variable electric temperature measurement signal, is provided in the medical or dental handpiece, in particular in its head section, and is connected in parallel electrically to the lighting device, wherein the shared electric line is provided for transmission of the temperature measurement signal. The temperature sensor is preferably electrically connected to the electric power source, for example, the constant current source or the constant voltage source, and in particular can be supplied with electric power by such a source.

The temperature sensor comprises, for example, a sensor having a material whose electric resistance is a function of temperature, in particular an NTC resistor or a PTC resistor, an infrared sensor or a thermocouple. The temperature sensor in particular is designed to determine the temperature of the handpiece, in particular the temperature in the interior of the handpiece and/or the temperature of at least one component of the handpiece. The temperature sensor is preferably arranged in or on or attached to a component of the handpiece, for example, the outer sleeve, the lighting device or a bearing. Alternatively, the temperature sensor is arranged freely in an interior space of the handpiece and is mounted substantially only on an electric signal line. The temperature sensor may have one or more sensors. The temperature sensor is designed to generate a temperature measurement signal, for example, by a change in a parameter of an electric power signal sent to the temperature sensor as a function of the temperature, for example, the amperage.

According to one embodiment, the constant current source or the constant voltage source of the medical or dental treatment device is designed to receive a mixed electric signal which comprises the variable electric temperature measurement signal generated by the temperature sensor and to correct this variable electric temperature measurement signal by means of a second variable electric correction signal, such that a substantially constant electric signal for the power supply to the lighting device is provided. Three electric power sources (the constant current source or the constant voltage source, the rotational speed measuring device and the temperature sensor) are thus especially preferably provided and their electric signals (the constant electric power supply signal, the variable electric rotational speed measurement signal and the variable electric temperature measurement signal) are superimposed and form the mixed electric signal and their electric signals are transmitted or are transmissible, in particular simultaneously, over the shared electric line.

An evaluation unit connected to the temperature sensor or to the constant current source or to the constant voltage source is preferably provided and is designed to determine the temperature measured by the temperature sensor on the basis of the temperature measurement signal or the second variable electric correction signal of the constant current source or the constant voltage source. A single evaluation unit (in the form of a microcontroller) is provided and is designed to determine the rotational speed of the drive element in particular on the basis of the first variable electric correction signal of the constant current source or the constant voltage source and to determine the temperature measured by the temperature sensor on the basis of the second variable electric correction signal of the constant current source or the constant voltage source.

The control unit and/or regulating unit is/are preferably designed to generate a warning signal on reaching or exceeding a temperature limit value and/or to interrupt the operation of the handpiece or of the treatment device or of the drive element.

The medical or dental treatment device preferably comprises a warning device or a display device which is designed to display the rotational speed of the drive element determined by the rotational speed measuring device and/or the temperature value determined by the temperature sensor. The display device is operatively connected to the control unit and/or the regulating unit in particular.

A method for operating a medical or dental handpiece is defined by the fact that the electric power (the electric power supply signal) for the lighting device and the rotational speed measurement signal of the rotational speed measuring device are transmitted over the at least one shared electric line.

A method for operating a medical or dental treatment device is defined by the method described above for operating a medical or dental handpiece, wherein the evaluation unit additionally determines the rotational speed of the drive element on the basis of the variable electric rotational speed measurement signal or the first variable electric correction signal of the constant current source or the constant voltage source. The constant current source or the constant voltage source preferably receives a mixed electric signal, which comprises the variable electric rotational speed measurement signal that is generated by the rotational speed measuring device and is assigned to the rotational speed of the drive element and corrects this variable electric rotational speed measurement signal by means of a first variable electric correction signal, such that the substantially constant electric signal for the power supply to the lighting device is provided. The control unit and/or regulating unit especially preferably controls and/or regulates the rotational speed of the drive element on the basis of the rotational speed determined by the evaluation unit and in particular by comparison of the rotational speed determined by the evaluation unit with a predetermined setpoint rotational speed, in particular such that the drive element is operated at a constant rotational speed. The evaluation unit preferably determines the temperature measured by the temperature sensor on the basis of the temperature measurement signal or of the second variable electric correction signal of the constant current source or the constant voltage source.

These and other embodiments will be described below with reference to the following drawings

DETAILED DESCRIPTION

Figures 1, 2:
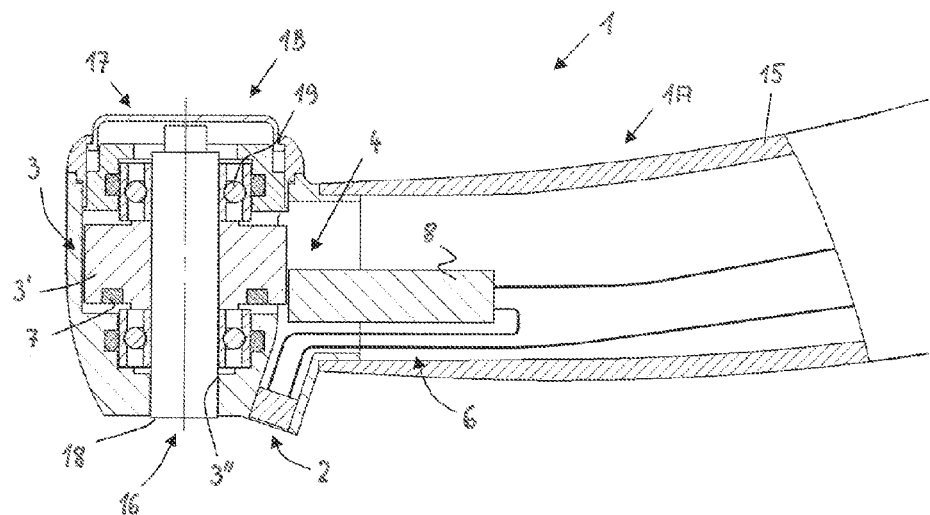
FIG. 1 shows an embodiment of a medical or dental handpiece having a shared electric line for the transmission of electric power to the lighting device and of a rotational speed measurement signal of a rotational speed measuring device.
FIG. 2 shows an embodiment of a medical or dental treatment device having a handpiece according to FIG. 1.

The medical or dental handpiece 1 of FIGS. 1 and 2 comprises a handle section 1A and a head section 1B. An outer sleeve 15 surrounds the handpiece. The handpiece 1 is designed as a handpiece operated with compressed gas, in particular compressed air, and comprises in its head section 1B a drive element 3, which can be set in rotation, in particular in the form of an impeller 3' that can be acted upon with compressed gas. The compressed gas can be supplied to the drive element 3 over a compressed gas line (not shown) extending through the handpiece 1. A shaft or a hollow shaft 3" is a part of or connected to the drive element 3 and is designed to receive a tool that can be connected to the handpiece 1. The hollow shaft 3" is thus also a part of a tool holding device 16 arranged in the head section 1B for releasable accommodation of a tool, in particular a drill that can be set in rotation. Two roller bearings 19 are provided for rotational support of the drive element 3 in the head section 1B. A tool receptacle opening 18 provided laterally on the head section 1B is connected to the tool holding device 16. A tool release device 17 is designed to release the tool from the tool holding device 16, so that it can be removed by a user.

A lighting device 2 for emitting radiation onto a treatment site is provided in an opening on the outer sleeve 15, preferably in the head section 1B, or connected thereto. The lighting device 2 comprises at least one light source to which electric power can be supplied, preferably at least one optical semiconductor element, for example, a light-emitting diode. Preferably a plurality of optical semiconductor elements can be arranged electrically in parallel or in series, in particular being positioned around the tool receptacle opening 18. An electric power source 11 (see FIGS. 2 and 3), for example, a constant current source and/or a constant voltage source is provided to supply a substantially constant electric signal, in particular a constant voltage or constant current or direct current 5', to the lighting device 2 (see FIG. 4).

To measure the rotational speed of the drive element 3, in particular of the impeller 3', a rotational speed measuring device 4 is provided in the handpiece 1. At least a portion of the rotational speed measuring device 4 is arranged near or adjacent to the drive element 3, preferably in the head section 1B of the handpiece 1. The rotational speed measuring device 4 of the handpiece 1 of FIG. 1 is designed as an inductive rotational speed measuring device having a magnetic element 7 and a measuring coil 8. The magnetic element 7 is preferably connected to the drive dement 3, in particular to the impeller 3' or alternatively to the shaft 3", such that it can be set in rotation with the drive element 3. The magnetic element 7 may have, for example, a ring-shaped or toroidal magnet or multiple individual magnetic elements. The measuring coil 8, which is preferably equipped with a soft magnetic core, is positioned close to the magnetic element 7 and in a rotationally fixed position with respect to the drive element 3. A relative movement between the magnetic element 7 and the measuring coil 8 is induced by the rotation of the drive element 3, and a sinusoidal or pulse-shaped electric alternating signal is generated inductively. The rotational speed measuring device 4 thus forms an electric power source, which generates a variable electric rotational speed measurement signal 5 assigned to the rotational speed of the drive element 3 (see FIG. 4).

Further, a shared electric line 6 is provided in the handpiece 1, which is designed for transmission of electric power or an electric power supply signal 5' to the lighting device 2 and of the rotational speed measurement signal 5 of the rotational speed measuring device 4. As shown in FIG. 1, the rotational speed measuring device 4 and the lighting device 2, in particular the measuring coil 8, are arranged in series electrically. The lighting device 2 and the measuring coil 8 are preferably attached directly to one another or to a shared carrier, for example, a circuit board.

FIG. 2 shows the design of a medical or dental treatment device 10 comprising the handpiece 1, an electric power source 11, for example, a constant current source or constant voltage source, which is designed to supply a substantially constant electric signal 5' to the lighting device 2, an evaluation unit 12, which is designed to determine the rotational speed of the drive element 3, and a control unit and/or a regulating unit 13, which is designed to control and/or regulate the rotational speed of the drive element 3 on the basis of the rotational speed determined by the evaluation unit 12. A clamping block (not shown) is preferably provided, connecting at least the electric lines of the lighting device 2 and the rotational speed measuring device 4, optionally also connecting further components that can be operated with electric power. A single microcontroller is preferably provided, comprising at least the evaluation unit 12 and the control unit and/or regulating unit 13. In particular the evaluation unit 12 and the control unit and/or regulating unit 13, preferably also the electric power source 11, may be arranged in a supply unit 20 that is preferably detachable from the handpiece 1. The supply unit 20 preferably also comprises a connection to a compressed air source and optionally also to other media sources, for example, to a water supply. A supply hose 21 and a coupling device 22, which is detachable in particular, connect the supply unit 20 to the handpiece 1. In particular the shared electric line 6 and/or an electric line connected thereto extend(s) through the handpiece 1, the coupling device 22 and the supply hose 21 up to the electric power source 11, the evaluation unit 12 or the control unit and/or regulating unit 13.

Figure 3:
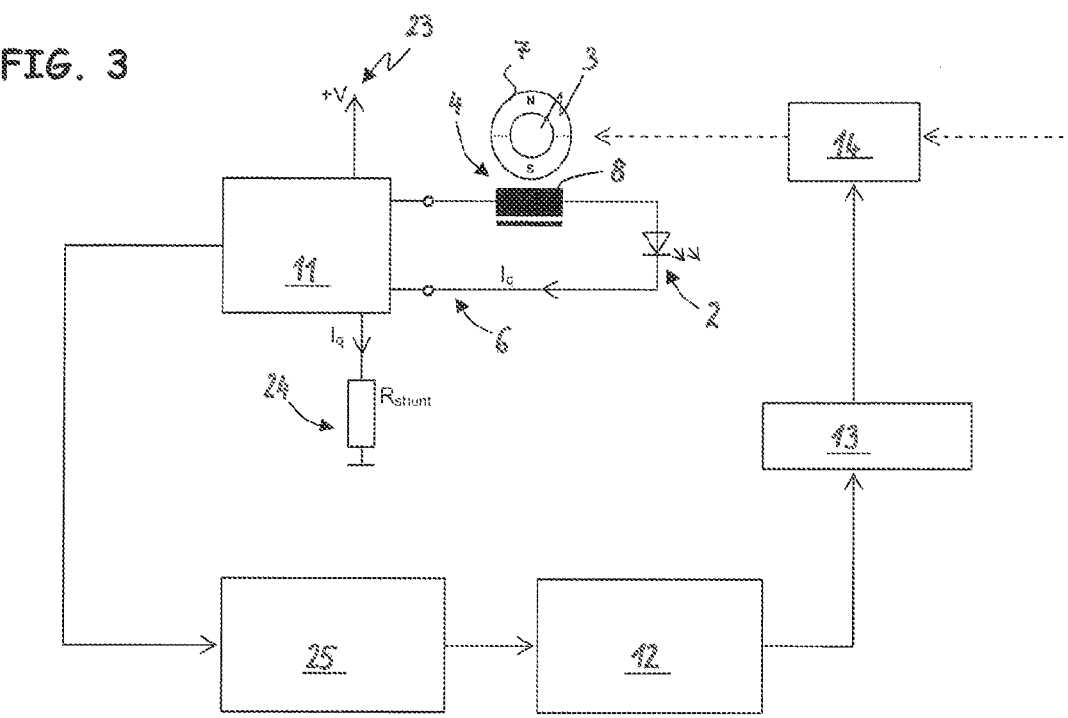
FIG. 3 shows a schematic diagram of an electric control or regulating circuit for controlling or regulating the rotational speed of a drive element having a shared electric line for transmission of electric power to the lighting device and of a rotational speed measurement signal of a rotational speed measuring device.
Figure 4:
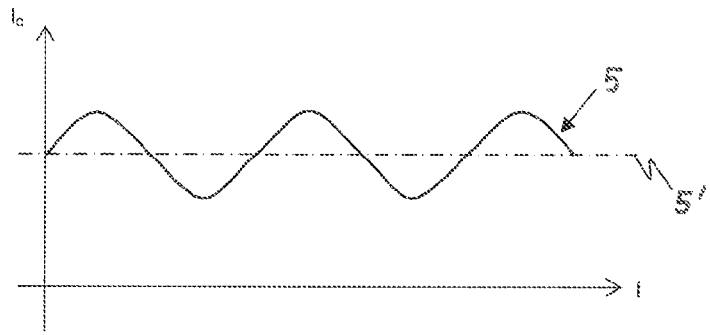
FIG. 4 shows in a schematic diagram the composition and the characteristic of a mixed electric signal over time, comprising the variable electric rotational speed measurement signal generated by the rotational speed measuring device and assigned to the rotational speed of the drive element, and comprising the substantially constant electric signal supplied by the electric power source to supply power to the lighting device.

FIG. 3 shows a schematic diagram of an electric control or regulating circuit for control or regulation of the rotational speed of the drive element 3. The diagram shows the components already described in conjunction with the handpiece 1, i.e., the lighting device 2, the drive element 3, the rotational speed measuring device 4 with the measuring coil 8 and the magnetic element 7 as well as the shared electric line 6. An electric power source of the treatment device 10 comprises the constant current source 11 and a constant voltage source 23, wherein the two electric sources 11, 23 are preferably connected to one another electrically. The constant current source 11 and/or the constant voltage source 23 is/are designed to supply electric power (the substantially constant electric signal 5') to the lighting device 2 via the measuring coil 8 and the shared electric line 6. The constant voltage source or the constant current source 11 is also designed as an electric or electronic regulating device in particular, which regulates the electric power supply to the lighting device 2 substantially at a predefined level of the constant voltage or constant current 5', preferably together with a shunt resistor 24.

If the drive element 3 and the magnetic element 7 connected to it are set in rotation, the rotational speed measuring device 4 generates, as described above, a variable electric rotational speed measurement signal 5, which is applied to the shared electric line 6. The shared electric line 6 thus conducts a mixed electric signal, comprising the variable electric rotational speed measurement signal 5 which is generated by the rotational speed measuring device 4 and is assigned to the rotational speed of the drive element 3 and the substantially constant electric signal 5' (see FIG. 4). In other words, the constant electric signal 5' and the variable electric rotational speed measurement signal 5 are superimposed and form the mixed electric signal.

The constant current source or the constant voltage source 11 is designed to receive the mixed electric signal and to correct its variable (sinusoidal or pulse-shaped) component, i.e., the variable electric rotational speed measurement signal 5, by means of a first variable electric correction signal, such that the substantially constant electric signal 5' for the power supply to the lighting device 2 is provided. The evaluation unit 12, which is electrically connected to the constant current source or the constant voltage source 11, is designed to determine the rotational speed of the drive element 3 on the basis of the first variable electric correction signal of the constant current source or the constant voltage source 11 or to determine the rotational speed of the drive element 3 directly on the basis of the variable electric rotational speed measurement signal 5. The evaluation unit 12 is preferably designed to detect or pick up the first variable electric correction signal of the constant current source or the constant voltage source 11 or the variable electric rotational speed measurement signal 5 and in particular to determine the rotational speed of the drive element 3 on the basis of the frequency of the first correction signal or of the rotational speed measurement signal 5. The frequency of the correction signal corresponds to the frequency of the rotational speed measurement signal 5 of the rotational speed measuring device 4. Preferably at least one device 25 for processing the first correction signal or the rotational speed measurement signal 5, for example, an analog-digital converter or a signal filter is connected upstream to the evaluation unit 12 or is designed as part of it.

The evaluation unit 12 is electrically connected to a control unit and/or regulating unit 13. The control unit and/or regulating unit 13 is designed to control and/or regulate the rotational speed of the drive element 3 on the basis of the rotational speed determined by the evaluation unit 12, in particular such that the drive element 3 can be operated at a constant rotational speed. The control or regulation is preferably accomplished by comparing the rotational speed determined by the evaluation unit 12 with a predefined setpoint rotational speed. Preferably, an adjusting element is provided which is connected to the control unit and/or regulating unit 13 and is designed for specifying a setpoint rotational speed value. The control unit and/or regulating unit 13 comprises an adjusting element 14 or is connected to an adjusting element 14, which is designed to act on the compressed gas driving the drive element 3. The adjusting element 14 is designed in particular as a valve, for example, as a proportional valve or a solenoid valve. The adjusting element 14 is in particular designed to adjust the gas pressure and/or the volume flow of the compressed gas.

Figure 5:
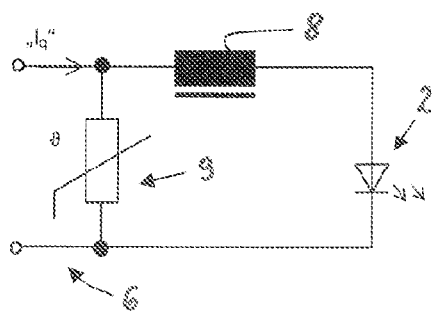
FIG. 5 shows a schematic diagram of a detail of an electric control or regulating circuit to control or regulate the rotational speed of a drive element and to measure the temperature, wherein a shared electric line is provided for transmission of electric power to the lighting device, for transmission of a rotational speed measurement signal of a rotational speed measuring device and for transmission of a temperature measurement signal of a temperature sensor.

FIG. 5 shows a schematic diagram of a detail of an electric control or regulating circuit for control or regulation of the rotational speed of a drive element 3 and for measuring the temperature, wherein a shared electric line 6 is provided for transmission of electric power to the lighting device 2, a rotational speed measurement signal 5 of a rotational speed measuring device 4 and a temperature measurement signal of a temperature sensor 9. The temperature sensor 9 is arranged in parallel electrically with the lighting device 2 and with the measuring coil 8 of the rotational speed measuring device 4. Moreover, the control or regulating circuit of FIG. 5 corresponds in design and function to the control or regulating circuit of FIG. 3, wherein the constant current source or constant voltage source 11 is designed to receive a mixed electric signal, which also comprises, in addition to the rotational speed measurement signal 5 of the rotational speed measuring device 4, the variable electric temperature measurement signal generated by the temperature sensor 9, and to correct this variable electric temperature measurement signal by means of a second variable electric correction signal, such that the substantially constant electric signal 5' is provided for the power supply to the lighting device 2. Further, the evaluation unit 12 is designed to determine the temperature measured by the temperature sensor 9 on the basis of the second variable electric correction signal of the constant current source or a constant voltage source 11 in addition to determining the rotational speed of the drive element 3.

The invention is not limited to the embodiments described here but instead includes all embodiments that apply or include the basic analogous function principle of the invention. In addition, all the features of all the embodiments described and illustrated here can be combined with one another.

What is claimed is:

1. A medical or dental handpiece, comprising:
   a rotatable drive element to drive a tool that can be connected to the handpiece,
   a rotational speed measurement device which is designed to generate a variable electric rotational speed measurement signal assigned to a rotational speed of the drive element,
   a lighting device that can be supplied with electric power for emitting radiation onto a treatment site, and
   at least one shared electric line, which is configured (1) to transmit electric power to the lighting device and (2) to transmit the rotational speed measurement signal of the rotational speed measurement device.

2. The medical or dental handpiece according to claim 1, wherein the rotational speed measurement device comprises one of: a capacitive rotational speed measurement device, an optical rotational speed measurement device, and an inductive rotational speed measurement device.

3. The medical or dental handpiece according to claim 1, wherein the lighting device and the rotational speed measurement device are arranged electrically in series.

4. The medical or dental handpiece according to claim 1, comprising a temperature sensor which is arranged electrically in parallel with the lighting device and is designed to generate a variable electric temperature measurement signal, wherein the shared electric line is further configured to transmit the temperature measurement signal.

5. The medical or dental handpiece according to claim 1, wherein the drive element comprises a rotor that can be driven by a compressed gas.

6. The medical or dental treatment device according to claim 1, wherein the at least one shared electric line connects the lighting device and at least a part of the rotational speed measuring device to an electric power source.

7. A medical or dental treatment device, comprising:
a medical or dental handpiece according to claim 1, and
an electric power source configured to supply a substantially constant electric signal to the lighting device.

8. The medical or dental treatment device according to claim 7, comprising an evaluation unit for determining the rotational speed of the drive element on the basis of at least one of: the variable electric rotational speed measurement signal generated by the rotational speed measurement device; and a variable electric correction signal generated by the electric power source.

9. The medical or dental treatment device according to claim 8, comprising a control- and/or regulating unit which is designed to control and/or to regulate the rotational speed of the drive element based on the rotational speed determined by the evaluation unit.

10. The medical or dental treatment device according to claim 7, wherein the electric power source comprises an electric or electronic regulating device.

11. A micro-controller operated method for determining the rotational speed of the drive element of a medical or dental handpiece, wherein the medical or dental handpiece comprises a rotational speed measurement device to generate a variable electric rotational speed measurement signal assigned to the rotational speed of the drive element and at least one shared electric line in the medical or dental handpiece, the method comprising:
transmitting electric power for the lighting device for emitting radiation onto a treatment site over the at least one shared electric line; and
transmitting a rotational speed measurement signal of the rotational speed measurement device towards an evaluation unit over the at least one shared electric line.

12. An electric control or regulating circuit for controlling or regulating the rotational speed of a drive element of a medical or dental handpiece, wherein the electric control or regulating circuit has a shared electric line for shared transmission of electric power of a first electric power source and an electric signal of a second, different electric power source, wherein the first electric power source comprises an electric power source for supplying power to a lighting device of the medical or dental handpiece and the second electric power source comprises a rotational speed measuring device of the medical or dental handpiece so that over the shared electric line (1) electric power can be transmitted to the lighting device of the medical or dental handpiece and (2) an electrical rotational speed measurement signal can be transmitted from the rotational speed measuring device of the medical or dental handpiece.

13. The electric control or regulating circuit according to claim 12, wherein at least a portion of the shared electric line is arranged in the medical or dental handpiece.

14. The electric control or regulating circuit according to claim 12, wherein the electric power source for supplying power to a lighting device comprises a constant current source and/or a constant voltage source which is designed to supply the lighting device with a substantially constant electric signal.

15. The electric control or regulating circuit according to claim 12, wherein the shared electric line connects the electric power source for supplying power to the lighting device with the lighting device and wherein the shared electric line connects the rotational speed measuring device with the electric power source for supplying power to the lighting device to transmit the electrical rotational speed measurement signal of the rotational speed measuring device to the electric power source for supplying substantially constant power to the lighting device.

16. The electric control or regulating circuit according to claim 14, wherein the constant current source and/or a constant voltage source comprises an electric or electronic regulating device.

17. The electric control or regulating circuit according to claim 12, further comprising an evaluation unit for determining the rotational speed of the drive element on the basis of at least one of: the rotational speed measurement signal generated by the rotational speed measurement device; a variable electric correction signal generated by the electric power source for supplying power to a lighting device.

18. The electric control or regulating circuit according to claim 12, wherein the lighting device and the rotational speed measurement device are arranged electrically in series.

19. The electric control or regulating circuit according to claim 12, wherein the electric power which is transmitted to the lighting device of the medical or dental handpiece and the electrical rotational speed measurement signal are transmitted over the shared electric line superimposed and/or simultaneously.

* * * * *